United States Patent
Honkura et al.

(10) Patent No.: US 8,257,081 B2
(45) Date of Patent: Sep. 4, 2012

(54) DENTURE ATTACHMENT, DENTURE AND PROCESS FOR PRODUCING THE SAME

(75) Inventors: Yoshinobu Honkura, Aichi (JP); Kazuo Arai, Aichi (JP)

(73) Assignee: Aichi Steel Corporation, Tokai-shi (JP)

( * ) Notice: Subject to any disclaimer, the term of this patent is extended or adjusted under 35 U.S.C. 154(b) by 1331 days.

(21) Appl. No.: 10/546,059

(22) PCT Filed: Sep. 3, 2004

(86) PCT No.: PCT/JP2004/012851
§ 371 (c)(1),
(2), (4) Date: Aug. 18, 2005

(87) PCT Pub. No.: WO2005/023140
PCT Pub. Date: Mar. 17, 2005

(65) Prior Publication Data
US 2006/0160048 A1    Jul. 20, 2006

(30) Foreign Application Priority Data
Sep. 5, 2003  (JP) .................................. 2003-314499

(51) Int. Cl.
*A61C 13/235* (2006.01)
(52) U.S. Cl. ......................................................... 433/189
(58) Field of Classification Search .................. 433/172, 433/189, 177–178
See application file for complete search history.

(56) References Cited

U.S. PATENT DOCUMENTS

| | | | | |
|---|---|---|---|---|
| 4,184,252 A | * | 1/1980 | Krol et al. ..................... | 433/172 |
| 4,530,663 A | * | 7/1985 | Portnoy ........................ | 433/189 |
| 4,626,213 A | * | 12/1986 | Shiner et al. .................. | 433/173 |
| 4,815,975 A | * | 3/1989 | Garrel et al. .................. | 433/189 |
| 4,957,438 A | * | 9/1990 | Bax ................................ | 433/180 |
| 4,993,950 A | * | 2/1991 | Mensor, Jr. .................... | 433/173 |
| 5,123,843 A | * | 6/1992 | Van der Zel et al. ......... | 433/189 |
| 5,254,006 A | * | 10/1993 | Yamada ........................ | 433/189 |
| 5,417,570 A | * | 5/1995 | Zuest et al. .................... | 433/177 |
| 5,421,722 A | * | 6/1995 | Stemmann .................... | 433/189 |
| 5,611,689 A | * | 3/1997 | Stemmann .................... | 433/189 |
| 5,871,357 A | * | 2/1999 | Tseng ............................ | 433/189 |
| 6,203,325 B1 | * | 3/2001 | Honkura et al. .............. | 433/177 |

FOREIGN PATENT DOCUMENTS

| | | |
|---|---|---|
| EP | 0 993 809 A1 | 4/2000 |
| FR | 1 493 464 | 9/1967 |
| FR | 2 587 895 | 3/1987 |
| FR | 2 718 948 | 10/1995 |

(Continued)

*Primary Examiner* — Cris L Rodriguez
*Assistant Examiner* — Hao D Mai
(74) *Attorney, Agent, or Firm* — Oblon, Spivak, McClelland, Maier & Neustadt, L.L.P.

(57) ABSTRACT

A dental attachment is embedded in a denture base so as to attach to a keeper made of a soft magnetic material built in a tooth root by magnetic attractive force. The dental attachment comprises an attachment main body which has a magnetic body delivering magnetic attractive force and a cap which covers a head portion located on the opposite side of an attractive surface to attach the keeper of the attachment main body. The cap, made of a non-magnetic material, is installed in the attachment main body so as to be able to move between a contacting position (A) which contacts with the head portion and an extended position (B) which is far from the head portion for a certain distance.

10 Claims, 10 Drawing Sheets

FOREIGN PATENT DOCUMENTS

| | | |
|---|---|---|
| JP | 6-86715 | 12/1994 |
| JP | 07-136190 | 5/1995 |
| JP | 9-154856 | 6/1997 |
| JP | 10-323356 | 12/1998 |
| JP | 2000-308648 | 11/2000 |
| JP | 2002-282281 | 10/2002 |

\* cited by examiner

DENTURE ATTACHMENT, DENTURE AND PROCESS FOR PRODUCING THE SAME

TECHNICAL FIELD

The present invention relates to a dental attachment which is used to embed a denture by magnetic attractive force, and a denture which is comprised using such a dental attachment, and a method of manufacturing thereof.

BACKGROUND

In dental treatment, as shown in patent document 1, Japanese Unexamined Patent Application No. 7-136190, because of the easiness of putting on or taking off the denture, various dental attachments utilizing magnetic attractive force have been proposed. A dental attachment 91, which has a magnetic body, is, as shown in FIG. 10, embedded in a denture base 810, which is fixed with an artificial tooth 81. On the side of a tooth root, a keeper 92 made of a soft magnetic material is embedded in a root cap 82 or an implant (the embodiment is abbreviated) is embedded. Therefore the denture, which has the dental attachment 91, can be fixed to the keeper 92 by magnetic attractive force.

As shown FIG. 11 and FIG. 12, in a denture 9 in which are planted a plurality of the artificial teeth 81 in the denture base 810, an artificial tooth 81a corresponding to the place where the dental attachment is embedded and an artificial tooth 81b corresponding to the place where the dental attachment 91 is not embedded, that is not to face the keeper 92, exist.

Until now, after a denture is made, the denture is put in a oral space for about two weeks without the dental attachment (magnetic assembly) built in the denture and when the shrinkage of a gingiva is stabilized, a dentist has combined the dental attachment to the denture. So stress to a gingiva where the dental attachment works is alleviated. But in about half a year, the gingiva gradually shrinks and modification of the denture and recombination of the dental attachment are needed.

On the other hand, dentists desire that the dental attachment should be combined with the denture in the making process before dentists work to put the dental attachment into the denture. However, if the combination is done in the making process, it is unpredictable where and how much gingiva shrinks. Therefore, if the denture, which is combined with the dental attachment in a conventional making process, is put on for about a week, stress to the gingiva is concentrated and a strange feeling or ache is generated.

In more detail, if the denture which is made and completed on the model is used, because the denture is not adequately adapted to the oral space, due to occluding stress, the artificial tooth 81b and the denture base 810 supporting it begin to shrink according to the shape change of the tooth gingiva 88. Meanwhile, the embedded dental attachment 91 cannot shrink because the keeper 92 and dental attachment 91 exist. Therefore, occluding stress is concentrated on the artificial tooth 81a, which is embedded according to the location of the embedded dental attachment 91, and it causes a strange feeling or ache to the patient with the denture 9.

Therefore, especially in the case of combining the dental attachment to the denture in the making process, development of the dental attachment which has a function to alleviate stress to the gingiva has been desired. Also, the development of the manufacturing method of the denture with the dental attachment has been desired.

[patent document 1]: Japanese Unexamined Patent Application Publication No. 7-136190 [patent document 2]: Japanese Unexamined Utility Model Application Publication No. 6-86715

SUMMARY OF THE INVENTION

The present invention provides a dental attachment which can restrain the concentration of occluding stress to the part where the dental attachment is combined even after long use, a denture using that dental attachment, and its manufacturing method.

A first aspect of the present invention relates to a dental attachment configured to be embedded in a denture base so as to attach to a keeper made of a soft magnetic material and embedded in a tooth root. The dental attachment comprises an attachment main body which has a magnetic body delivering magnetic attractive force, and a cap covering a head portion which is located on the side opposite to an attractive surface to attach the keeper of the attachment main body. The cap is made of a non-magnetic material and engaged to the attachment main body so as to be able to move between a contacting position which, contacts with the head portion and an extended position which, is far from the head portion for a certain distance.

The dental attachment of the present invention has, as mentioned above, a cap, which is movable between the connecting position and the extended position. Therefore, the whole denture containing the cap can move to the attachment main body. Therefore, even if the place where a keeper and attachment main body is connected is fixed, the whole denture with the cap can be moved relative to the keeper within the certain distance. Therefore, even if the denture is made on a model, the denture with the dental attachment can be moved according to the change of the shape of the gingiva. Therefore, the denture with the dental attachment can restrain the concentration of occluding stress even if it is completed on the model in the making process.

Especially, it is not necessary to put the denture in the oral space for about two weeks to stabilize the shrinkage of the gingiva after the conventional denture without the dental attachment is made. So, it is possible to complete the denture with the dental attachment on the model in the making process. Also, the necessity to modify the denture and recombine the dental attachment is reduced. Yet also it is needless to say that even in the case that without combining the dental attachment to the denture in the making process, the dentist combines the dental attachment to the denture after stabilizing the shrinkage of the gingiva in the conventional way, and the necessity to modify the denture and recombine the dental attachment can be reduced.

The attachment main body (sometimes called a magnet assembly) may have any well-known structure. Also, the keeper, which is combined to the dental attachment, may have any well-known structure. Furthermore, an attractive surface on the dental attachment, as shown in the following embodiment, may be flat, may have a convex face, or may have a concave face with a set curvature.

A second aspect of the present invention is a denture having the above-described dental attachment embedded in a denture base to attach a keeper made of a soft magnetic material in a tooth root and an artificial tooth planted in the denture base. The dental attachment includes an attachment main body which has a magnetic body delivering magnetic attractive force and a cap which covers a head portion which is located on the side opposite to an attractive surface to attach the keeper of the attachment main body. The cap is made of a non-magnetic material and engaged to the attachment main body so as to be able to move between a contacting position which contacts with the head portion and an extended position which is far from the head portion for a certain distance. The cap is held in the denture base and the attachment main body is installed so as to be able to move to the cap.

The denture of the present invention has the constituted dental attachment. As mentioned above, the denture base holds the cap and the attachment main body is embedded so as to be able to be movable to the cap. Therefore, if at the beginning of use, the attachment main body is moved forward and set so as to make a gap between the head portion and the cap, the cap moves forward relative to the attachment main body after use and the placement position of the denture can be changed. Thus, as mentioned above, the denture of the present invention can restrain the concentration of occluding stress at the combining part of the dental attachment.

A third aspect of the present invention is a method of manufacturing the above described denture having a dental attachment embedded in a denture base to attach a keeper made of a soft magnetic material in a tooth root and an artificial tooth planted in the denture base. The dental attachment includes an attachment main body, which has a magnetic body delivering magnetic attractive force and a cap covering a head portion, which is located on the side opposite to an attractive surface to attach the keeper of the attachment main body. The cap is made of a non-magnetic material and attached to the attachment main body so as to be able to move between a contacting position, which contacts with the head portion, and an extended position, which is far from the head portion for a certain distance. Another aspect of the invention includes a process of manufacturing a denture body including the denture base, the artificial tooth planted in the denture base, and a recess so as to insert the dental attachment in the denture base. This aspect further includes a process of manufacturing a keeper side model which has the keeper in a casts plaster model which imitates a gingival shape including the tooth root. Also included is a process of setting the dental attachment, in which a spacer with a thickness within the range in which the cap of the dental attachment can move is installed, and in which the dental attachment is installed so that the spacer is contacted to a disk, and in which also the cap of the dental attachment is installed in the contacting position. Also included is a process of fixing the dental attachment, in which the denture body is covered on the keeper side model so as to house the dental attachment in the recess with an adhesive applied inside.

In one example of the method of manufacturing the dental attachment of the present invention, at least the process of manufacturing the denture body, the process of manufacturing the keeper side model, the process of setting the dental attachment, and the process of fixing the dental attachment are performed. One notable part of the manufacturing method is that before fixing the dental attachment, the spacer is intervened on the keeper side model on the keeper, and has the setting process of the dental attachment, which is the dental attachment is embedded in the state of arranging the cap in the connecting position.

By practicing the contacting process of the dental attachment after setting the dental attachment using this spacer, the dental attachment embedded in the denture base has a structure with a gap of the thickness of the spacer between the keeper and attachment main body with the state that the head portion of the attachment main body abuts against the cap. Therefore, when the denture is put on the denture base of the same shape as the keeper model and started to be used, the attachment main body moves forward relative to the keeper and is magnetically connected with the keeper when the attachment main body faces to the keeper. Thus, a gap of the thickness of the spacer exists between the face of the head portion of the attachment main body and the cap. After that, as mentioned above, the cap moves forward relative to the attachment main body using the gap, according to the change of the shape of the gingiva. So, the placement location of the denture changes and the concentration of occluding stress can be restrained.

DETAILED DESCRIPTION

Figure 1:
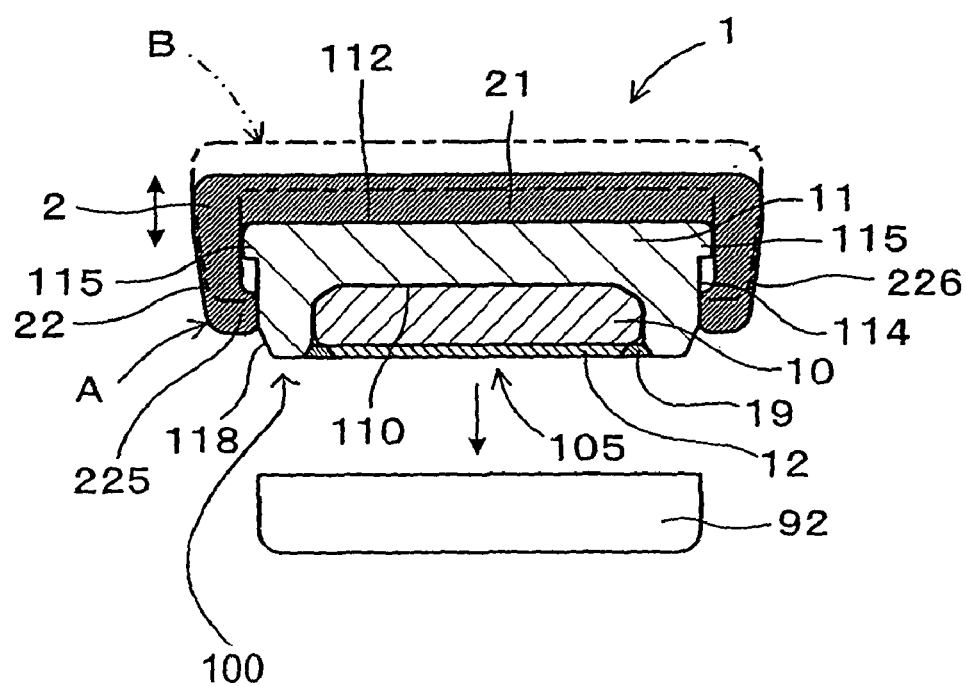
FIG. 1 is an illustration of the structure of the dental attachment of the first embodiment.

According to one example of the dental attachment of the present invention, it is preferable that the attachment main body includes the magnetic body, a yoke made of the soft magnetic material with a concave part which has the magnetic body, a disk made of the soft magnetic material which is installed so as to close a opening part of the concave part with the magnetic body housed in the concave part, and ring shaped contacting part made of the non-magnetic material which connects the disk and the yoke, and the cap is covered on the head portion which is located on the opposite side to the opening part of the yoke. In this case, the yoke, the disk and the ring shaped connecting part between these can form an ideal magnetic circuit and magnetic force of the magnetic body can be utilized efficiently.

The non-magnetic material constituting the yoke can be various soft magnetic materials, for instance, 17Cr stainless steel, 17Cr-2Mo stainless steel, and 19Cr-2Mo stainless steel are preferable. These are superior in non-corrosion and can improve the endurance. Also, as the soft magnetic material for the disk, various soft magnetic materials are available and the same materials as the yoke can be used. Still, the connection of the disk and the yoke is practiced on the ring shaped connecting part made of the non-magnetic material. As a specific connecting method, welding is applicable. Also, as the magnetic body built in the yoke, a magnet with high magneto motive force per unit volume is used. Specifically, for instance, Sm—Co based, Nd—Fe—B based, or rare earth magnets with high-energy product are preferable.

Further, it is preferable that the attachment main body has collars protruding radially outward from an outer peripheral surface thereof, and the cap has a bottom portion which faces the head portion of the attachment main body and a lateral portion which faces the outer peripheral surface of the attachment main body and covers the collars, and the lateral portion has a protruding part protruding inward to the outer peripheral surface of the yoke and the protruding part and the collars are engaged when the cap is located at the extended position. By this structure, relative movement between the cap and the attachment main body is possible and the moving distance between the collars and the inward protruding part can be easily controlled by attaching them.

Further, it is preferable that the outer peripheral surface of the lateral portion of the cap has a tapered surface reducing radially away from the bottom portion and/or an outward-protruding part. In this case, when the denture is held in the denture base, the taper face or an outer protruding part bites and delivers the undercut effect, so the attaching strength of both can be improved.

Further, it is preferable that the cap is made of synthetic resin. In this case, by using flexibility of the synthetic resin constituting the cap, the operation to attach with the attachment main body can be done easily and the manufacturing becomes simpler. As the synthetic resin, for instance, POM (polyoxymethylene), PE (polyethylene), PET (polyethylene terephthalate) etc. can be used.

Next, according to the third aspect of the invention, it is preferable that the spacer is made of a permanent magnet or the soft magnetic material. In this case, when the spacer is equipped on the keeper, the location between both can be maintained stably, and also when the dental attachment is equipped on the spacer, the location between both can be maintained stably. Therefore, afterward the process of fixing the dental attachment can be stably done.

Embodiment 1

A first embodiment of a dental attachment of the present invention is explained using FIG. 1. A dental attachment 1 of this example is, as shown in FIG. 1, a dental attachment which is embedded in a denture base so as to be conjugated to a keeper 92 made of a soft magnetic material in a tooth root by magnetic attractive force.

The dental attachment 1 includes an attachment main body 100, which has a magnetic body 10 delivering magnetic attractive force and a cap 2 covering a head portion 112 which is located on the side opposite to an attractive surface 105 to attach the keeper 92 of the attachment main body 100. The cap 2, made of a non-magnetic material and attached to the attachment main body 100 so as to be able to move between a connecting position (A) which contacts with the head portion 112 and an extended position (B) which is far from the head portion for a certain distance.

The attachment main body 100 includes, as shown in FIG. 1 the magnetic body 10 delivering magnetic attractive force, a yoke 11 made of the soft magnetic material which has a recess 110 housing the magnetic body 10, a disk 12 which covers an opening part of the recess 110 with the magnetic body 10 housed in the recess, and a ring shaped connecting part 19, made of the non-magnetic material, which connects the disk 12 with the yoke 11. The cap 2 covers the head portion 112 which is the opposite side to the opening part of the yoke 11.

As shown in FIG. 1, the yoke 11 of the dental attachment in this embodiment is almost disk shaped and has collars 115 protruding radially outward from the outer peripheral surface 114. In the depicted embodiment, collars 115 are present all over the outer peripheral surface 114 at the edge of the head portion 112. However, collars 115 can be made, for instance, at circumferentially plural separated locations.

Also, the yoke 11 is made of the soft magnetic material, 19Cr-2Mo-0.2Ti—Fe, and made by machining. The yoke 11 has the recess 110 to house the magnetic body 10 by machining. The inner diameter of this recess 110 corresponds to the outer diameter of the magnetic body 10 described later. Also, the corner of the outer periphery of the face, which has the recess 110, a taper shaped chamfer 118 is shown.

In the depicted sample, the magnetic body 10 is made of Nd—Fe—B based permanent magnet, (BH)max=42MGOe. The disk 12 is a circular disk made of the soft magnetic material, 19Cr-2Mo-0.2Ti—Fe, for example. After the magnetic body 10 is inserted in the recess 110 of the yoke 11, the disk 12 is inserted and the outer peripheral thereof is welded to the yoke 11 with the ring shaped connecting part 19 made of the non-magnetic material.

The cap 2 has a bottom portion 21 which faces the head portion 112 of the yoke 11 and a lateral portion 22 which faces the outer peripheral surface 114 and covers the collars 115. The lateral portion 22 has a protruding part 225 protruding inward to the outer peripheral surface 114 of the yoke 11 and the protruding part and the collars 115 are engaged when the cap 2 is located at the extended position (B).

Also, the cap 2 has, as shown in the same FIG, a taper face 226 which has a smaller diameter as it is further away from the bottom portion 21 at the outer peripheral face of the lateral portion 22. In addition, the cap 2 is made of POM (polyoxymethylene) and mounted on the yoke 11 from the side of the head portion 112 of the yoke 11.

The obtained dental attachment 1 has the cap 2, which is movable between the connecting part (A) and the extended part (B), and is structured to be changeable to the relative position between the cap 2 and the yoke 11. Because of this structure, the denture with the cap 2 attached in the denture base can change the relative position of the whole denture to the yoke 11 (the attachment main body 100), and excellent operating effects can be obtained.

Embodiment 2

Figure 2:
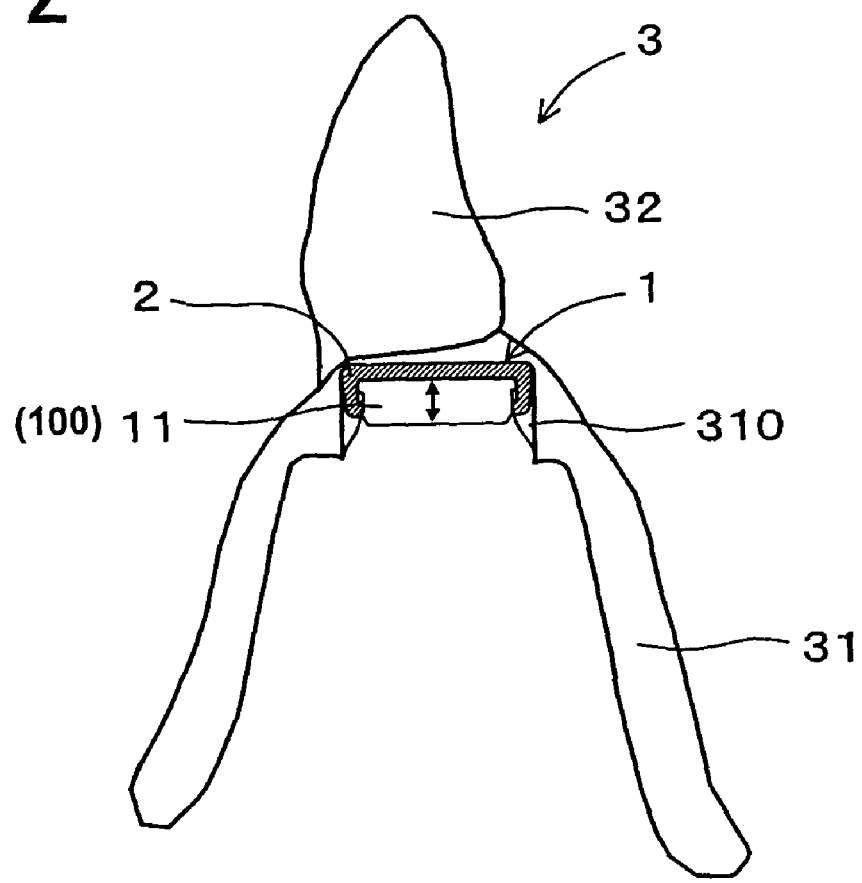
FIG. 2 is an illustration of the structure of the denture of the second embodiment.

In the present example, as shown in FIGS. 2-5, a denture which is made by using the dental attachment of embodiment 1, and the manufacturing method, are explained. A denture 3 of the present embodiment consists, as shown in FIG. 2, of an artificial tooth 32 planted in a denture base 31 and the dental attachment 1 of embodiment 1 in the denture base 31. The cap 2 is held in the denture base 31 and the yoke 11 (the attachment main body 100) can be movable to the cap 2.

Figure 3:
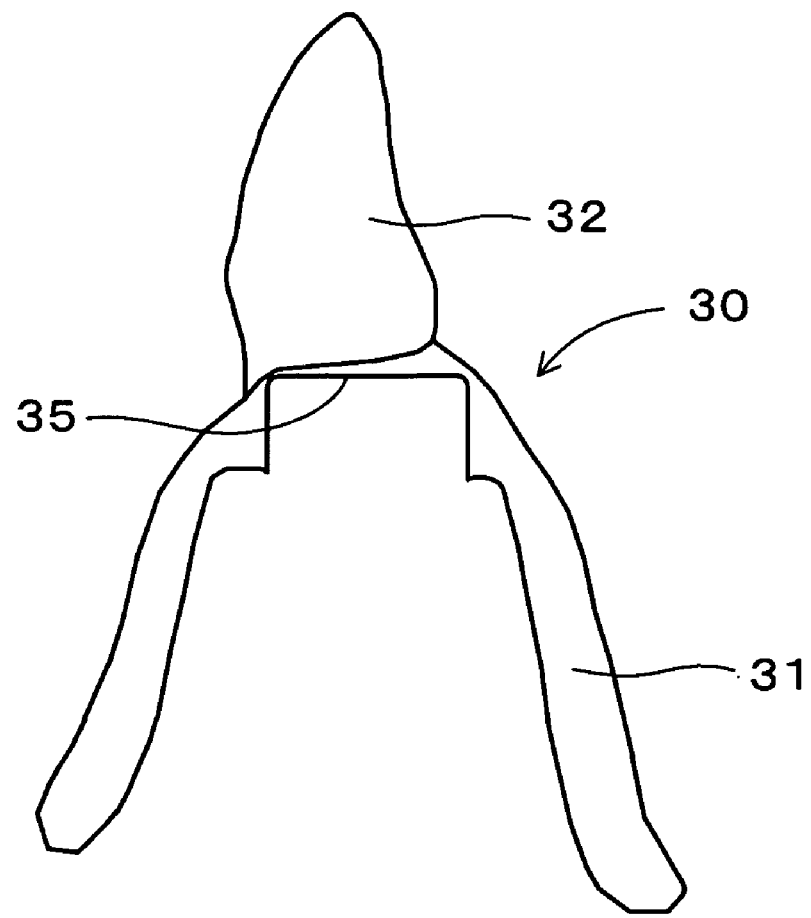
FIG. 3 is an illustration of the structure of the denture body of the second embodiment.
Figure 4:
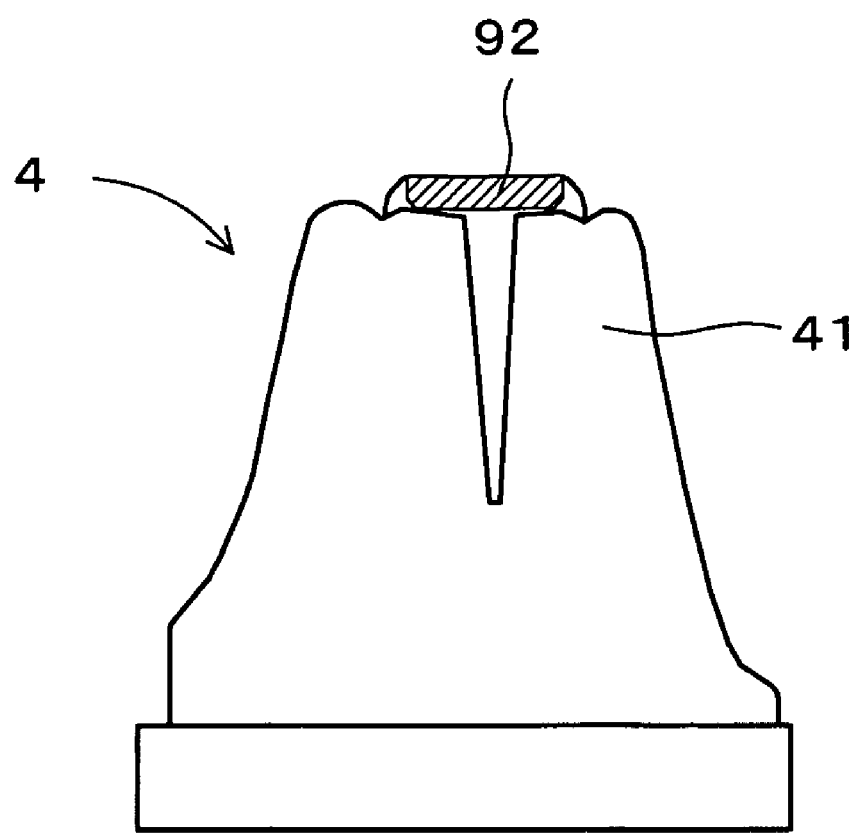
FIG. 4 is an illustration of the structure of the keeper side model of the second embodiment.

The first step to manufacture this denture is, as shown in FIG. 3, the artificial tooth 32 is planted in the denture base 31 and a denture body 30 which has a recess 35 to insert the dental attachment 1 in the denture base 31 is manufactured. Also, as shown in FIG. 4, a keeper side model 4 which is embedded a keeper 92 in a casts plaster model 41 which imitates the gingival shape including a tooth root part to install a denture 3 is manufactured. The manufacturing process of this keeper side model can be done before or after the manufacturing process of the denture body and both process can be done in parallel.

Also, in the process of manufacturing the denture body or the keeper side model, the process of impression taking which transfers the shape of the gingiva including the tooth root part to install the denture is needed. Using prior instant adhesive or gypsum can do the process of impression taking.

Figure 5:
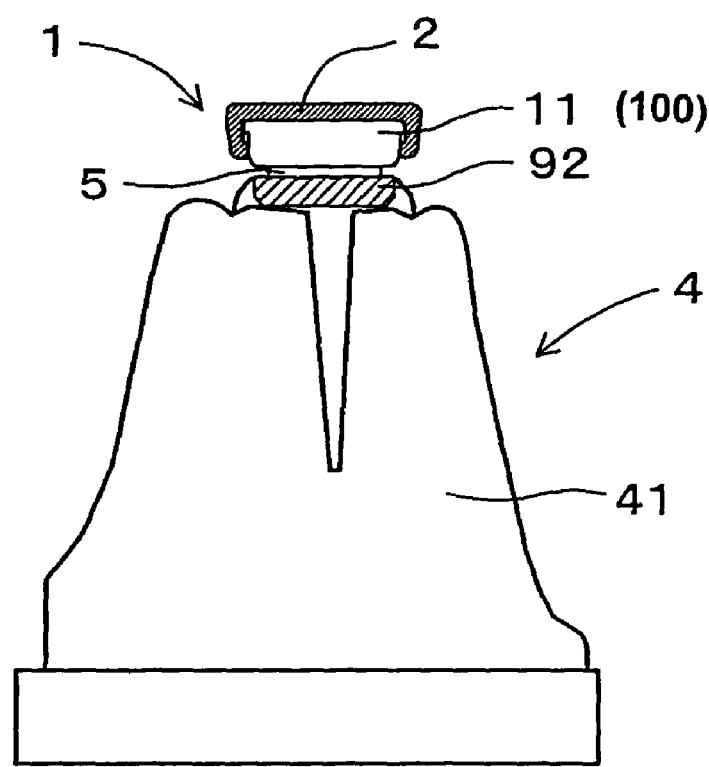
FIG. 5 is an illustration showing a state in which the spacer and dental attachment are set on the keeper side model of the second embodiment.

Next, as shown in FIG. 5, preparing a disk shaped spacer 5 which is made of a ferrite magnet and has almost the same thickness of the moving distance of the cap 2 of the dental attachment 1, the setting process of the dental attachment is done. Specifically, as shown in the same FIG, first, the spacer 5 is installed on the keeper 92 of the keeper side model 4, and on it, the dental attachment 1 on which is installed the cap 2 at the connecting position is installed. At this time, the disk 12 is connected with the spacer 5. In the present example, as mentioned above, the spacer 5 is made of the permanent magnet, so the keeper 92, the spacer 5 and the dental attachment 1 are stably installed.

Figure 6:
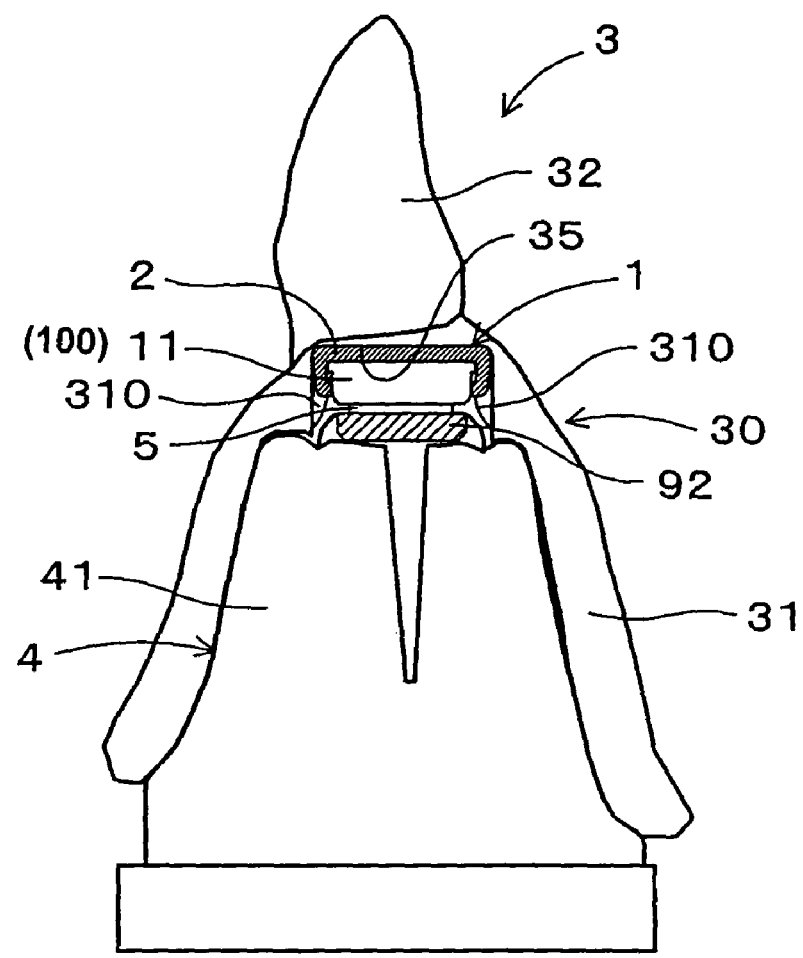
FIG. 6 is an illustration showing a state of the process of fixing the dental attachment of the second embodiment.

Next, as shown in FIG. 6, an adhesive 310 is applied inside the recess 35 of the denture body 30 and the process of fixing the dental attachment which covers the keeper side model 4 with the denture body 30 in order to house the dental attachment 1 in the recess 35 is conducted. Thus, as shown in the same FIG, the cap 2 of the dental attachment 1 is attached in the recess 35 with the adhesive 310, completing the denture 3 which has the dental attachment 1.

Figure 7:
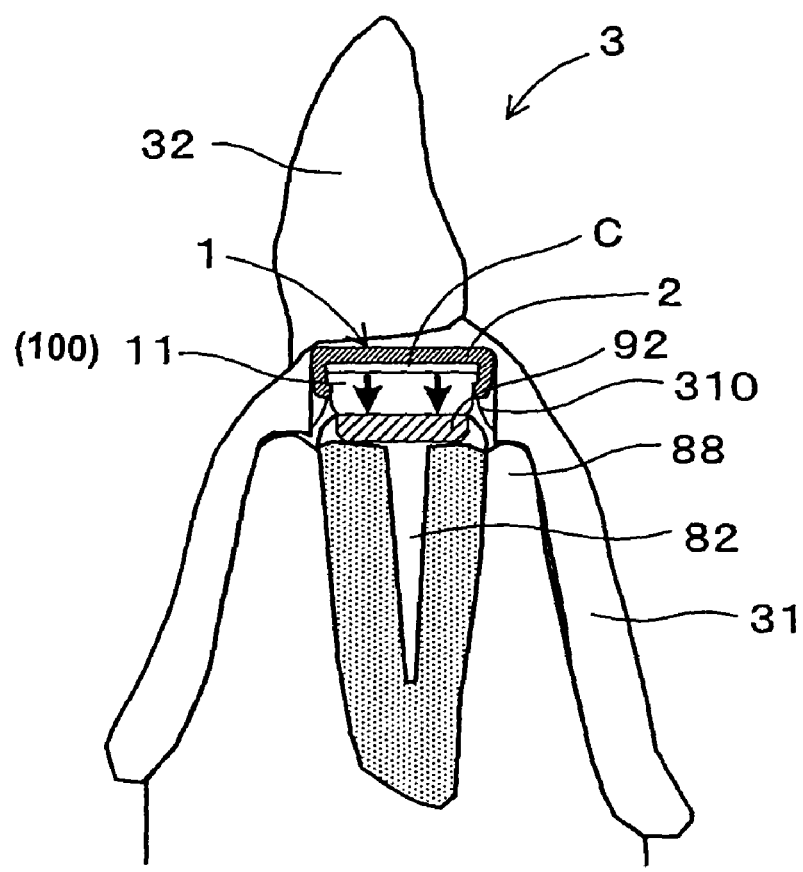
FIG. 7 is an illustration showing a state of beginning to use the dental attachment actually of the second embodiment.

In the obtained denture 3, the cap 2 of the installed dental attachment 1 is attached and the yoke 11 (the attachment main body 100) is held to be movable to the cap 2. The starting point of the yoke 11 is set at the advanced point of the thickness of the spacer 5 from the connecting point of the yoke 11 with the cap 2, where the yoke 11 connects with the keeper 92. Therefore, as shown in FIG. 7, when the keeper 92 is embedded in a real gingiva 88, which is an original of the keeper side model 4, and the denture 3 is put on it, as shown in the same FIG, the yoke 11 advances relative to the cap 2 and contacts the keeper 92 and is connected. Therefore, at the starting step of usage, a certain amount of a gap C is made between the cap 2 and the yoke 11 and it become a space which adapts to the subsequent change over time.

That is, in the case that the gingiva 88 begins to shrink, the denture base 31 also begins to shrink. At this time, the dental attachment 1 of the present example, as mentioned above, can move relatively so as to shrink the gap C between the yoke 11 and the cap 2. Therefore, the denture 3 can follow the change of the gingiva 88's shrinking and move to a suitable position. Therefore, in the denture 3 of the present embodiment, even in the case that the gingiva 88 etc. is changed by time, the concentration of occluding stress on the combining part of the dental attachment can be restrained.

As the denture 3, a denture with a plurality of artificial teeth is especially effective, but a denture with only one artificial tooth 32 can also be excellently effective to deliver the operating effect of the dental attachment 1.

Embodiment 3

Figure 8:
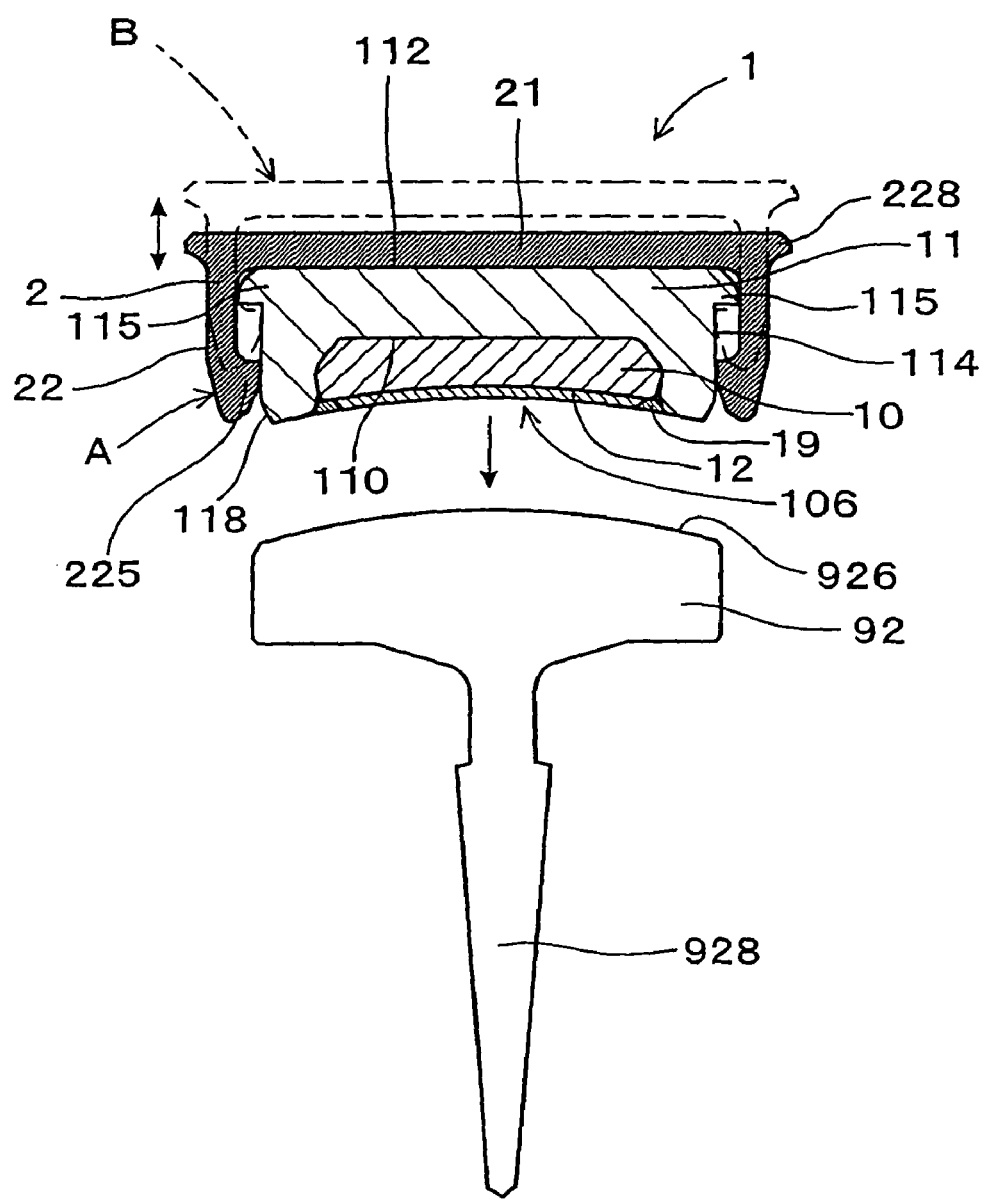
FIG. 8 is an illustration of the structure of the dental attachment of the third embodiment.

The present example is an example of changing the shape etc. of the dental attachment of FIG. 8 and embodiment 1. As shown in FIG. 8, first, an attractive surface 106 is made of a concave surface (spherical face) of an attachment main body 100. As a keeper 92 facing the attachment main body 100, an absorbed surface 926 which is made of a convex surface (spherical face) and can be attached to an attractive surface 106 is adopted. The keeper 92 has a post 928 which is extended from the back center on the opposite side of the absorbed surface 926.

The cap 2 which covers the head portion 112 of the attachment main body 100 has cap collars 228 protruding outward at all outer peripheral surfaces of a lateral portion 22. In other respects of the structure is the same as embodiment 1.

The dental attachment of the present example, which has the concave attractive surface 106 as mentioned above, can be used in combination with the keeper 92 which has the convex absorbed surface 926. Therefore, the attaching condition of the attractive surface 106 and the absorbed surface 926 is maintained and can be inclined from the starting condition. For some kinds of the dentures, adopting this structure is very effective.

In the present example, the cap 2 has the cap collars 228. Thus, when the cap 2 is connected to a denture base 31 with an adhesive 310, the cap collars 228 is embedded in the adhesive 310 and the connecting strength between the cap 2 and the denture base 31 can be improved. However, the cap collars 228 need not be made all around and a shape with at least one radially protruding part is possible. It also obtains the same operating effect as embodiment 1.

Embodiment 4

Figure 9:
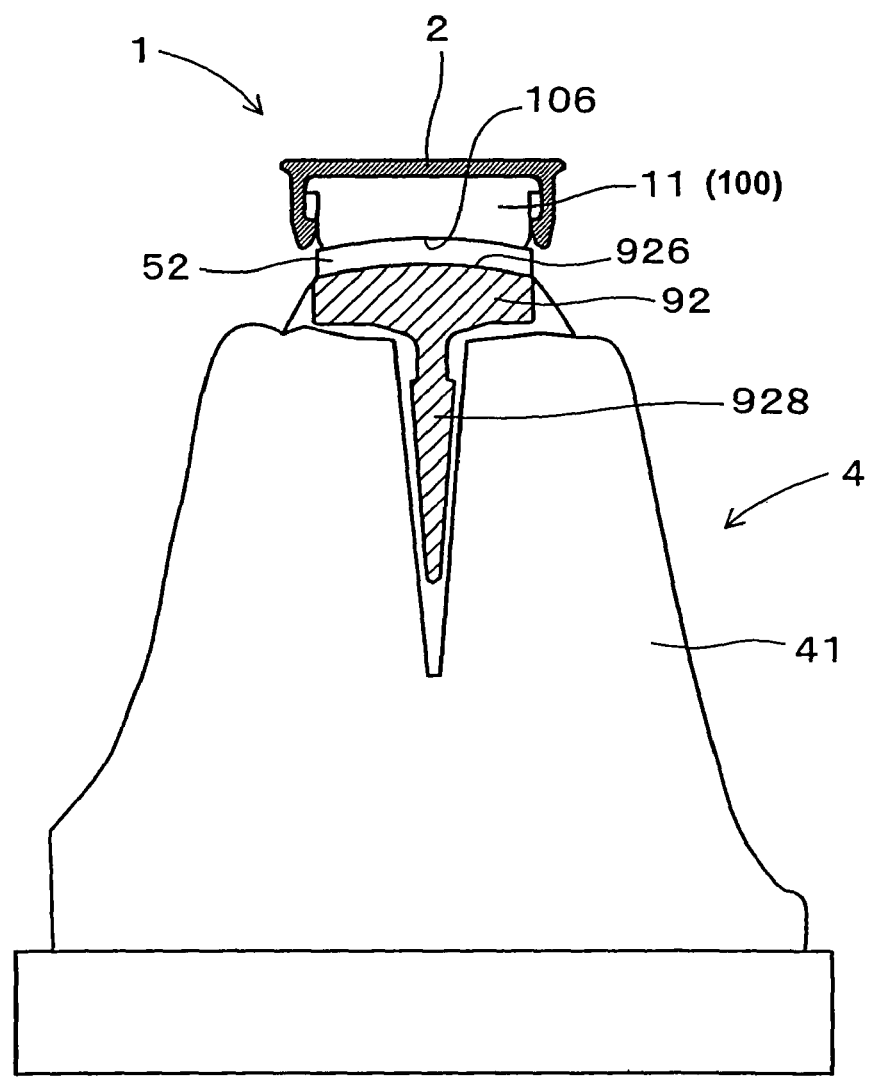
FIG. 9 is an illustration showing a state of setting a spacer and dental attachment on the keeper side model of the fourth embodiment.
Figure 10:
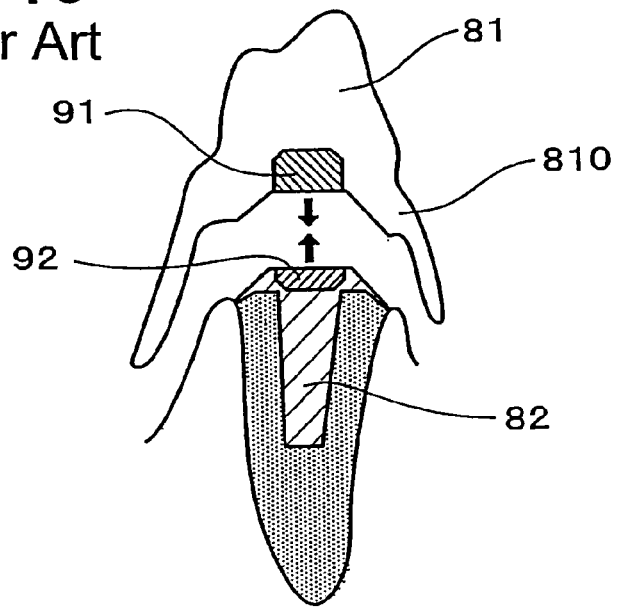
FIG. 10 is an illustration of the state of using a dental attachment in the prior art.
Figure 11:
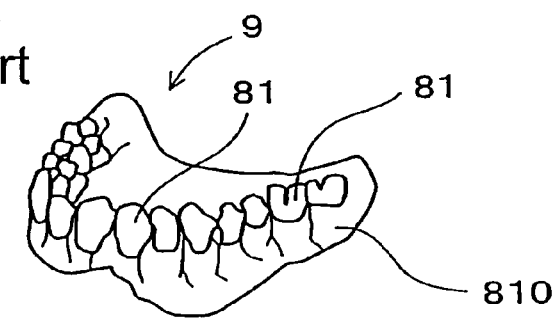
FIG. 11 is an illustration of a denture in the prior art.
Figure 12:
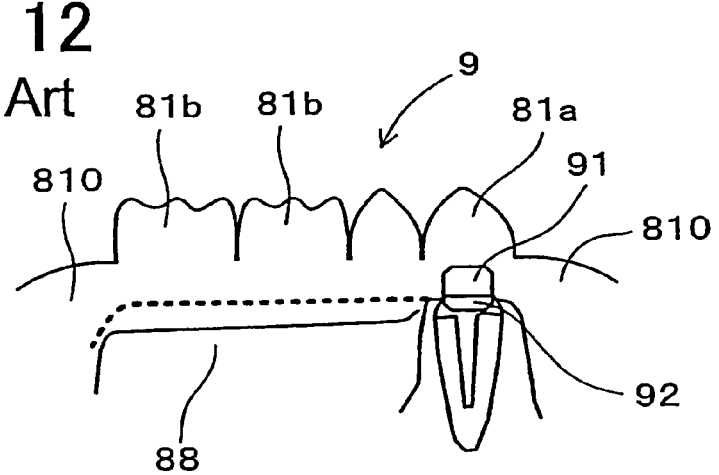
FIG. 12 is an illustration of a bad state in the prior art.

In the present example, as shown in FIG. 9, the manufacturing method of a denture is explained by using the dental attachment of embodiment 3. The manufacturing method of the present example, which is basically the same as embodiment 2, is changed in the shape and materials of a spacer 52. That is, first, like embodiment 2, a process of manufacturing a denture body 30 which makes the denture body 30 and a process of manufacturing a keeper side model which makes a keeper side model 4 embeds a keeper 92 in a casts plaster model 41 is performed.

Next, as shown in FIG. 9, a process of setting the dental attachment is performed by using the disk shaped spacer 52 which is made of the soft magnetic material, 19Cr-2Mo-0.2Ti, and has the thickness of about the same as the moving distance of the cap 2 of the dental attachment 1 and has a spherical shape with the same curvature as the attractive surface 106 of the attachment main body 100 and the absorbed surface 926 of the keeper 92. The spacer 52 and the absorbed surface 926 are connected with an adhesive. The process afterward is the same as embodiment 2.

As mentioned above, in the present example, the dental attachment, which has the concave attractive surface 106, can be easily installed in the denture body 30 by using the disk shaped spacer 52 with spherical shape. It also obtains the same operating effect as embodiment 2.

The invention claimed is:
1. A dental attachment configured to be embedded in a denture base so as to attach to a keeper by a magnetic attractive force, the keeper including a soft magnetic material and embedded in a tooth root, comprising:
   an attachment main body including a magnetic body delivering magnetic attractive force; and
   a cap covering a head portion of the attachment main body and located on a side of the magnetic body opposite to an attractive surface that attaches to the keeper,
   wherein the cap includes a non-magnetic material and is coupled to the attachment main body so as to be configured to move, while remaining coupled to the attachment main body, between a contacting position (A) at which the cap is in contact with the head portion and an extended position (B) spaced from the contacting position (A) by a distance, a space being provided between the head portion and the cap, in the extended position,
   wherein the attachment main body further includes
   a yoke, a portion of the outer peripheral surface of the yoke being straight and without a taper, the yoke including soft magnetic material with a concave part which accommodates the magnetic body, a disk including soft magnetic material which is installed so as to close an opening part of the concave part while the magnetic body is housed in the concave part, and a ring shaped contacting part including the non-magnetic material which connects the disk and the yoke, wherein the cap covers the head portion, which is located on an opposite side of the yoke to the opening part of the concave part of the yoke, wherein the yoke has a collar and a cylindrical outer peripheral surface, said collar protrudes radially outward from the cylindrical outer peripheral surface of the yoke at the edge of the head portion of the yoke, and the cap includes a bottom portion, which faces the head portion of the yoke, and a lateral portion, which faces the cylindrical outer peripheral surface of the yoke and covers the collar, and the lateral portion includes a protruding part protruding inward to the cylindrical outer peripheral surface of the yoke, and the protruding part and the collar are engaged when the cap is located at the extended position (B) and said protruding part and said collar are not engaged when said cap is located at said contacting position (A), and wherein the cap is configured to move, without bias generated by the dental attachment, from the extended position (B) to the contacting position (A) and vice versa.

2. The dental attachment according to claim 1, wherein an outer peripheral surface of the lateral portion of the cap includes a tapered surface reducing radially away from the bottom portion and/or an outward-protruding part.

3. The dental attachment according to claim 1, wherein the cap includes synthetic resin.

4. The dental attachment according to claim 1, wherein the cap is configured to freely move from the extended position (B) to the contacting position (A) and vice versa by movement along the portion of the yoke that is straight.

5. The dental attachment according to claim 4, wherein the yoke includes a tapered portion, and the portion of the yoke that is straight is positioned between the tapered portion and the collar.

6. A dental attachment configured to be embedded in a denture base so as to attach to a keeper by a magnetic attractive force, the keeper including a soft magnetic material and embedded in a tooth root, comprising:

an attachment main body including a magnetic body delivering magnetic attractive force; and a cap covering a head portion of the attachment main body and located on a side of the magnetic body opposite to an attractive surface that attaches to the keeper, wherein the cap includes a non-magnetic material and is coupled to the attachment main body so as to be configured to move, while remaining coupled to the attachment main body, between a contacting position (A) at which the cap is in contact with the head portion and an extended position (B) spaced from the contacting position (A) by a distance, a space being provided between the head portion and the cap, in the extended position, wherein the attachment main body further includes a yoke, a portion of the outer peripheral surface of the yoke being straight and without a taper, the yoke including soft magnetic material with a concave part which accommodates the magnetic body, a disk including soft magnetic material which is installed so as to close an opening part of the concave part while the magnetic body is housed in the concave part, and a ring shaped contacting part including the non-magnetic material which connects the disk and the yoke, wherein the cap covers the head portion, which is located on an opposite side of the yoke to the opening part of the concave part of the yoke, wherein the yoke has a collar and a cylindrical outer peripheral surface, said collar protrudes radially outward from the cylindrical outer peripheral surface of the yoke at the edge of the head portion of the yoke, and the cap includes a bottom portion, which faces the head portion of the yoke, and a lateral portion, which faces the cylindrical outer peripheral surface of the yoke and covers the collar, and the lateral portion includes a protruding part protruding inward to the cylindrical outer peripheral surface of the yoke, and the protruding part and the collar are engaged when the cap is located at the extended position (B) and said protruding part and said collar are not engaged when said cap is located at said contacting position (A), and wherein the cap is configured to move to adjust to a gum line from the extended position (B) to the contacting position (A) and vice versa.

7. The dental attachment according to claim 6, wherein an outer peripheral surface of the lateral portion of the cap includes a tapered surface reducing radially away from the bottom portion and/or an outward-protruding part.

8. The dental attachment according to claim 6, wherein the cap includes synthetic resin.

9. The dental attachment according to claim 6, wherein the cap is configured to freely move from the extended position (B) to the contacting position (A) and vice versa by movement along the portion of the yoke that is straight.

10. The dental attachment according to claim 9, wherein the yoke includes a tapered portion, and the portion of the yoke that is straight is positioned between the tapered portion and the collar.

* * * * *